United States Patent [19]

Wirth et al.

[11] Patent Number: 5,071,898

[45] Date of Patent: Dec. 10, 1991

[54] PROPANE-1,3-DIONE DERIVATIVES AND THEIR USE AS STABILIZERS FOR POLYMERS CONTAINING CHLORINE

[75] Inventors: Hermann O. Wirth, Bensheim; Hans-Helmut Friedrich, Lautertal; Gerd Abeler, Darmstadt, all of Fed. Rep. of Germany

[73] Assignee: Ciba-Geigy Corporation, Ardsley, N.Y.

[21] Appl. No.: 360,801

[22] Filed: Jun. 2, 1989

[30] Foreign Application Priority Data

Jun. 6, 1988 [CH] Switzerland .................... 2139/88

[51] Int. Cl.$^5$ .................... C08K 5/13; C08K 5/07; C07C 49/17; C07C 49/337
[52] U.S. Cl. .................... 524/290; 524/306; 524/357; 568/336; 568/337; 568/413
[58] Field of Search .................... 524/357, 290, 306; 568/336, 337, 413

[56] References Cited

U.S. PATENT DOCUMENTS

| | | | |
|---|---|---|---|
| 3,001,970 | 9/1961 | Ebel et al. | 260/45.95 |
| 3,493,536 | 2/1970 | Weisfeld | 260/45.75 |
| 3,615,888 | 10/1971 | Wystrach et al. | 148/6.14 R |
| 3,816,615 | 6/1974 | Zeffren et al. | 424/62 |
| 4,123,399 | 10/1978 | Gay | 260/23 X A |
| 4,244,848 | 1/1981 | Minagawa et al. | 260/23 X A |
| 4,252,698 | 2/1981 | Ito et al. | 260/18 EP |
| 4,282,141 | 8/1981 | Minagawa et al. | 260/45.7 R |
| 4,381,360 | 4/1983 | Leistner et al. | 524/64 |
| 4,416,797 | 11/1983 | Minagawa et al. | 252/400 A |
| 4,427,816 | 1/1984 | Aoki et al. | 524/357 |
| 4,849,466 | 7/1989 | Michaelis | 524/105 |

FOREIGN PATENT DOCUMENTS

| | | |
|---|---|---|
| 035268 | 3/1981 | European Pat. Off. . |
| 55-84341 | 6/1980 | Japan . |
| 788428 | 1/1958 | United Kingdom . |

OTHER PUBLICATIONS

Kraus et al., J. Org. Chem., vol. 49, pp. 3212-3214 (1984).
Detty, J. Org. Chem., vol. 44, No. 13, pp. 2073-2077 (1979).
Cannan et al., J. Org. Chem., vol. 17, pp. 1245-1251 (1952).
Kappe et al., Eur. J. Med. Chem., Chimica Therapeutica, vol. 10, pp. 154-161 (1975).
Chemical Abstracts No. 71:49840d (1969).
Uchino et al. Tetrahedron Letters, vol. 26, pp. 1319-1320 (1985).
Chemical Abstracts No. 87:135221q (1977).

Primary Examiner—Veronica P. Hoke
Attorney, Agent, or Firm—JoAnn Villamizar

[57] ABSTRACT

Composition containing a) a polymer containing chlorine and b) at least one compound of the formula I

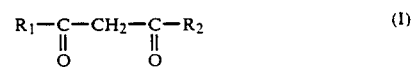
(I)

in which $R_1$ is $C_1$-$C_{10}$alkyl, $C_2$-$C_{10}$hydroxyalkyl, phenyl, hydroxyphenyl, $C_7$-$C_{10}$phenylalkyl or $C_7$-$C_{10}$phenylalkyl which is substituted on the phenyl ring by an OH group, and $R_2$ is $C_2$-$C_{10}$hydroxyalkyl, hydroxyphenyl or $C_7$-$C_{10}$phenylalkyl which is substituted on the phenyl ring by an OH group, subject to the condition that $R_2$ is other than hydroxyphenyl if $R_1$ is phenyl or hydroxyphenyl, and/or at least one compound of the formula I in which the OH groups present in the radicals $R_1$ and $R_2$ have been replaced by $C_2$-$C_{12}$alkanoyloxy.

The compounds of the formula IA

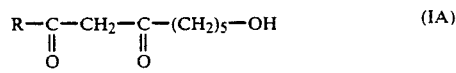
(IA)

in which R is $C_1$-$C_{10}$alkyl, $C_2$-$C_{10}$hydroxyalkyl, phenyl, hydroxyphenyl, $C_7$-$C_{10}$phenylalkyl or $C_7$-$C_{10}$phenylalkyl which is substituted on the phenyl ring by an OH group, are novel.

14 Claims, No Drawings

PROPANE-1,3-DIONE DERIVATIVES AND THEIR USE AS STABILIZERS FOR POLYMERS CONTAINING CHLORINE

The present invention relates to chlorine-containing polymers stabilized against thermal degradation by propane-1,3-dione derivatives, to the use of propane-1,3-dione derivatives as stabilizers and to novel propane-1,3-dione derivatives.

It is known that polymers containing chlorine have to be protected against the harmful effect of light and heat, particularly when being processed to give shaped articles. 1,3-diketones and the use thereof as stabilizers are disclosed, for example, in U.S. Pat. No. 3,493,536, U.S. Pat. No. 4,123,399, U.S. Pat. No. 4,244,848, U.S. Pat. No. 4,252,698, U.S. Pat. No. 4,282,141, U.S. Pat. No. 4,381,360, GB-A 788,428 and EP-A 35,268.

The preparation of 1,3-diketones is also described in detail in a number of publications. The following may be mentioned as representative publications: G. A. Kraus et al., J. Org. Chem. 49, 3212-3214 (1984) and M. R. Detty, J. Org. Chem. 44, 2074-2077 (1979).

The use of 1,3-diketones as starting materials for the preparation of heterocyclic compounds is described in the following publications: G. W. Cannon et al., J. Org. Chem. 17, 1245-1251 (1952), V. Koppe et al., Eur. J. Med. Chem.-Chimica Therapeutica 10, 154-161 (1975), Chemical Abstracts 71:49840d (1969), K. Uchino et al., Tetrahedron Letters 26, 1319-1320 (1985).

The treatment of metal surfaces with 1,3-diketones is described in U.S. Pat. No. 3,615,888, and U.S. Pat. No. 3,816,615 discloses hair bleaches containing 1,3-diketones.

Chemical Abstracts 87:135221q (1977) discloses the compound 7-hydroxy-5,5-dimethylheptane-2,4-dione.

The present invention relates to compositions containing a) a polymer containing chlorine and b) at least one compound of the formula I,

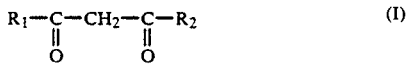

in which $R_1$ is $C_1-C_{10}$alkyl, $C_2-C_{10}$hydroxyalkyl, phenyl, hydroxyphenyl, $C_7-C_{10}$phenylakyl or $C_7-C_{10}$phenylalkyl which is substituted on the phenyl ring by an OH group, and $R_2$ is $C_2-C_{10}$hydroxyalkyl, hydroxyphenyl or $C_7-C_{10}$phenylalkyl which is substituted on the phenyl ring by an OH group, subject to the condition that $R_2$ is other than hydroxyphenyl if $R_1$ is phenyl or hydroxyphenyl, and/or at least one compound of the formula I in which the OH groups present in the radicals $R_1$ and $R_2$ have been replaced by $C_2-C_{12}$alkanoyloxy.

Examples of $R_1$ as $C_1-C_{10}$alkyl are methyl, ethyl, n-propyl, isopropyl, n-butyl, tert-butyl, n-pentyl, n-hexyl, n-heptyl, n-octyl or n-decyl. $C_1-C_4$alkyl, in particular methyl and tert-butyl, is preferred.

Examples of $R_1$ and $R_2$ as $C_2-C_{10}$hydroxyalkyl are 2-hydroxyethyl, 3-hydroxypropyl, 4-hydroxybutyl, 2-hydroxybutyl, 5-hydroxypentyl, 1,1-dimethyl-3-hydroxypropyl, 6-hydroxyhexyl, 8-hydroxyoctyl and 10-hydroxydecyl. 2-Hydroxyethyl, 5-hydroxypentyl, 6-hydroxyhexyl and 7-hydroxyheptyl are preferred. The hydroxyalkyl group is preferably not in the 1-position. $R_2$ is especially a group of the formula $-(CH_2)_n-OH$ in which n is an integer from 2 to 7. $R_2$ as 5-hydroxypentyl is of particular interest.

If $R_1$ and $R_2$ are hydroxyphenyl, the OH group can be in the ortho-, meta— or para-position. o-Hydroxyphenyl is preferred.

Examples of $R_1$ as $C_7-C_{10}$phenylalkyl are benzyl and 2-phenylethyl.

Examples of $R_1$ and $R_2$ as $C_7-C_{10}$phenylalkyl which is substituted on the phenyl ring by an OH group are (2-hydroxyphenyl)methyl, (3-hydroxyphenyl)methyl, (4-hydroxyphenyl)methyl, 2-(2-hydroxyphenyl)ethyl and 2-(4-hydroxyphenyl)ethyl.

Examples of $C_2-C_{12}$alkanoyloxy are acetoxy, propionyloxy, butyryloxy, pentanoyloxy, hexanoyloxy, heptanoyloxy, octanoyloxy, nonanoyloxy, decanoyloxy, undecanoyloxy or dodecanoyloxy.

Compositions of interest are those containing, as the component b), at least one compound of the formula I in which $R_1$ is $C_1-C_{10}$alkyl, $C_2-C_{10}$-hydroxyalkyl, phenyl, hydroxyphenyl, $C_7-C_{10}$phenylalkyl or $C_7-C_{10}$phenylalkyl which is substituted on the phenyl ring by an OH group, and $R_2$ is $C_2-C_{10}$hydroxyalkyl, hydroxyphenyl or $C_7-C_{10}$phenylalkyl which is substituted on the phenyl ring by an OH group, subject to the condition that $R_2$ is other than hydroxphenyl if $R_1$ is phenyl or hydroxyphenyl.

Preferred compositions are those containing, as the component b), at least one compound of the formula I in which $R_1$ is $C_1-C_{10}$alkyl, $C_2-C_{10}$-hydroxyalkyl or phenyl and $R_2$ is $C_2-C_{10}$hydroxyalkyl or hydroxyphenyl.

Compositions which are particularly preferred are those containing, as the component b), at least one compound of the formula I in which $R_1$ is $C_1-C_4$alkyl or phenyl and $R_2$ is $C_2-C_7$hydroxyalkyl or hydroxyphenyl.

Compositions which are also preferred are those containing, as the component b), at least one compound of the formula I in which $R_1$ is methyl, butyl or phenyl and $R_2$ is 2-hydroxyethyl, 5-hydroxypentyl, 6-hydroxyhexyl, 7-hydroxyheptyl or ortho-hydroxyphenyl.

Compositions in which the component b) is 1-phenyl-8-hydroxyoctane-1,3-dione, 1-t-butyl-8-hydroxyoctane-1,3-dione or 1-(o-hydroxyphenyl)butane-1,3-dione, especially 1-phenyl-8-hydroxyoctane-1,3-dione, are also of interest.

The polymers containing chlorine are preferably vinyl chloride homopolymers or copolymers. The following are examples of suitable comonomers for the copolymers: vinyl acetate, vinylidene chloride, trans-dichloro-ethylene, ethylene, propylene, butylene, maleic acid, acrylic acid, fumaric acid and itaconic acid. Other suitable chlorine-containing polymers are post-chlorinated PVC and chlorinated polyolefins, and also graft polymers of PVC with EVA, ABS and MBS. Preferred substrates are also mixtures of the abovementioned homopolymers and copolymers, in particular vinyl chloride homopolymers, with other thermoplastic and/or elastomeric polymers, in particular with ABS, MBS, NBR, SAN and EVA.

Suspension and bulk polymers and also emulsion polymers are also preferred.

Polyvinyl chloride is particularly preferred as the chlorine-containing polymer.

It is advantageous to employ the compounds of the formula I together with known heat stabilizers, for example Me(II) phenates, in particular $C_7-C_{20}$alkylphenates, for example nonylphenate, or Me(II) carboxylates. Me(II) is, for example, Ba, Ca, Mg, Cd or Zn. The carboxylates are preferably salts of carboxylic acids having 7 to 20 C atoms, for example benzoates, alkenoates or alkanoates, preferably stearates, oleates, laurates, palmitates, hydroxystearates or 2-ethylhexanoates. Stearates, oleates and p-tert-butylbenzoates are particularly preferred.

It is also preferable to employ the compounds of the formula I together with organotin compounds which are also known heat stabilizers. Examples of such organotin compounds are organotin carboxylates of the formulae indicated below

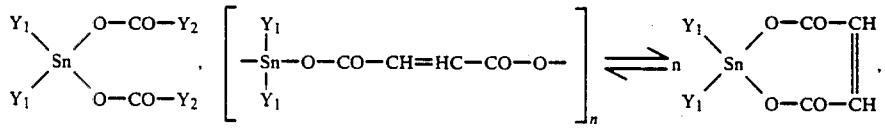

in which the radicals $Y_1$ independently of one another are $C_1-C_{12}$alkyl and the radicals $Y_2$ independently of one another are $C_1-C_{18}$alkyl or a group $-CH=CH-CO-O-(C_1-C_{18}alkyl)$.

Examples of alkyl are methyl, ethyl, propyl, butyl, pentyl, hexyl, heptyl, octyl, nonyl, decyl, undecyl, dodecyl, tridecyl, tetradecyl, pentadecyl, heptadecyl or octadecyl. $C_1-C_{10}$alkyl is preferred.

A particularly preferred organotin compound is

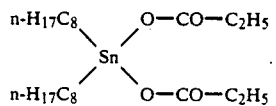

In addition, the chlorine-containing polymers can contain customary amounts of conventional PVC stabilizers, for example epoxy compounds, such as epoxidized oils and, preferably, epoxidized fatty acid esters, in particular epoxidized soya-bean oil, and also phosphites, preferably triorgano phosphites of the formula

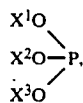

in which $X^1$, $X^2$ and $X^3$ independently of one another are $C_4-C_{18}$alkyl, phenyl or phenyl which is substituted by one to three $C_1-C_{12}$alkyl groups.

The invention preferably relates, therefore, to compositions containing not only the component a) and b) but, in addition, an epoxy compound and at least one Me(II) carboxylate and/or Me(II) phenate, in which Me(II) is Ba, Ca, Mg, Cd or Zn, and, if appropriate, a phosphite.

In accordance with a further preference the compositions according to the invention contain not only the component a) and b) but, in addition, epoxidized soya-bean oil and at least one Me(II) carboxylate, in which Me(II) is Ba, Ca, Mg or Zn. In this regard mixtures of Ba/Zn carboxylates or Ca/Zn carboxylates are particularly preferred as co-stabilizers.

The invention also preferably relates to compositions containing not only the component a) and b) but, in addition, an organotin compound and, if appropriate an Me(II) carboxylate, Me(II) being as defined above and being preferably Zn.

The known heat stabilizers (for example carboxylates, phenates or organotin compounds) can be present in the material to be stabilized in a concentration known to those skilled in the art, for example in amounts of 0.05 to 5% by weight.

The phosphites are employed in concentrations of, for example, 0.3 to 5, preferably 0.5 to 1, % by weight, and the epoxy compounds, for example epoxidized soya-bean oil, are employed in concentration of 1 to 8, preferably 1 to 3, % by weight.

The compounds of the formula I are incorporated in amounts of, for example, 0.05 to 1, preferably 0.1 to 0.5, % by weight, into the polymer containing chlorine.

The term % by weight relates in each case to the material to be stabilized.

Depending on the end use of the polymers, it is also possible, before or during the incorporation of the stabilizers, to incorporate further additives, for example phenolic antioxidants, lubricants (preferably montan waxes or glycerol esters), fatty acid esters, paraffins, plasticizers, fillers, carbon black, asbestos, kaolin, talc, glass fibres, modifiers (for instance impact modifiers), fluorescent brighteners, pigments, light stabilizers, UV absorbers, flame retardants or antistatic agents.

The incorporation of the stabilizer components into the polymer containing chlorine is effected most advantageously, in the customary manner, on a double roll mill at temperatures between 150° and 200° C. In general, adequate homogenization can be obtained within 5 to 15 minutes. The addition of the components can be effected individually or together in the form of a premix. A liquid premix has proved advantageous, i.e. processing is carried out in the presence of inert solvents and/or plasticizers.

The invention also relates to the novel compounds of the formula IA

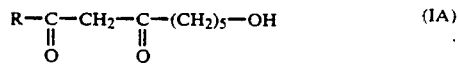

in which R is $C_1-C_{10}$alkyl, $C_2-C_{10}$hydroxyalkyl, phenyl, hydroxyphenyl, $C_7-C_{10}$phenylalkyl or $C_7-C_{10}$phenylalkyl which is substituted on the phenyl ring by an OH group.

Examples of R are the definitions indicated above for $R_1$.

R is preferably $C_1-C_{10}$alkyl, phenyl or $C_7-C_{10}$phenylalkyl, in particular $C_1-C_4$alkyl or phenyl.

Novel compounds of the formula IA which are particularly preferred are 1-phenyl-8-hydroxyoctane-1,3-dione and 1-t-butyl-8-hydroxyoctane-1,3-dione.

The compounds of the formulae I and IA can be prepared analogously to known processes, for example by reacting a compound of the formula II

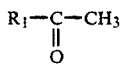

with a compound of the formula III,

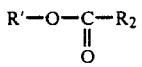

in which $R_1$ and $R_2$ are as defined above and $R'$ is preferably $C_1$-$C_3$alkyl, in the presence of a strongly basic compound, for example an alkali metal alcoholate, hydride or amide or a magnesium alcoholate, hydride or amide, in particular sodium methylate or sodium ethylate. The reaction is preferably carried out in an inert solvent, for example toluene, xylene or tetrahydrofuran, or in a mixture of solvents, for example di-n-butyl ether/dimethylformamide or di-n-butyl ether/tetrahydrofuran. The reaction temperature is preferably 5° to 25° C. The primary reaction product is the alkali metal chelate or magnesium chelate of the compound of the formula I, which can be split by acids, for example hydrochloric acid, sulfuric acid or formic acid. The corresponding compound of the formula I is then obtained. The crude product can subsequently be worked up by customary methods (for example recrystallization or distillation).

Compounds of the formula I in which $R_2$ is linear or branched $C_2$-$C_5$-hydroxyalkyl are preferably prepared by reacting a compound of the formula II with a lactone of formula IIIA

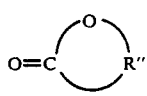

in which $R''$ is linear or branched $C_2$-$C_5$alkylene.

The reactions described above are known in the literature as a "CLAISEN condensation".

The compounds of the formula I in which the OH groups present in the radicals $R_1$ and $R_2$ have been replaced by $C_2$-$C_{12}$alkanoyloxy can be prepared by means of esterification reactions which are known to those skilled in the art.

The starting products are commercially available or can be prepared analogously to known processes.

The following examples illustrate the invention further. In these examples, parts and percentages are by weight, unless stated otherwise.

EXAMPLE 1

Preparation of 1-phenyl-8-hydroxyoctane-1,3-dione 75 g of a mixture of solvents are distilled off at normal pressure under a protective gas ($N_2$) from a mixture of 90 g of sodium methylate solution (30% in methanol) and 150 ml of di-n-butyl ether. The residue is cooled to 0° C. and 60 g of acetophenone and 100 ml of tetrahydrofuran are added dropwise at the same temperature. The mixture is stirred until a clear solution is present. 62.8 g of ε-caprolactone are then added dropwise in the course of 45 minutes at approx. 5° C. The reaction mixture is stirred for 30 minutes at the same temperature and stirring is then continued at 20° C. When the reaction is complete, the reaction mixture is hydrolyzed by means of 300 ml of ice water, and the organic phase is washed with 100 ml of water. The pH of the combined aqueous phases is adjusted to 6 with 50% sulfuric acid, and this solution is extracted with three times 70 ml of diethyl ether. The combined extracts are dried over $Na_2SO_4$ and concentrated to dryness on a rotary evaporator, the residue being a mass of yellowish crystals. The yield is 69.6 g (=59.4% of theory). After recrystallization from a mixture of di-n-butyl ether/toluene, the product has a melting point of 51°-52° C.

EXAMPLES 2–4

The compounds indicated in Table 1 are prepared analogously to the process described in Example 1.

TABLE 1

| Ex. | Compound | m.p./b.p. |
|---|---|---|
| 2 | Ph—C(=O)—CH₂—C(=O)—(CH₂)₃—OH | m.p. 45° C. |
| 3 | Ph—C(=O)—CH₂—C(=O)—CH₂—CH₂—CH(CH₃)—OH | m.p. 44° C. |
| 4 | $(H_3C)_3C$—C(=O)—CH₂—C(=O)—(CH₂)₅—OH | b.p. 99° C. (0.3 bar) |

EXAMPLE 5

Preparation of 1-(2'-hydroxyphenyl)butane-1,3-dione

The compound is prepared analogously to the process described by G. Wittig in "Berichte 58, 19 (1925)". Melting point: 90° C.

EXAMPLE 6

Preparation of 1-phenyl-8-acetoxyoctane-1,3-dione 6.1 g (0.06 mol) of acetic anhydride and 1 drop of concentrated sulfuric acid are initially placed in a 100 ml two-necked flask equipped with a magnetic stirrer and a thermometer. 11.7 g (0.05 mol) of the compound from Example 1 are added in portions, with stirring. The mixture is stirred for a further 30 minutes and is then diluted with 100 ml of diethyl ether. The mixture is then washed once with 100 ml of water, with twice 100 ml of bicarbonate and again once with 100 ml of water, dried and concentrated to dryness on a rotary evaporator, the residue being purified by distillation. The product obtained has a melting point of 23°–24° C.

EXAMPLE 7

Preparation of 1-phenyl-6-acetoxyhexane-1,3-dione 8.2 g (0.08 mol) of acetic anhydride and one drop of concentrated sulfuric acid are initially placed in a 100 ml two-necked flask equipped with a magnetic stirrer, a reflux condenser and a thermometer. 15.5 g (0.075 mol) of the compound from Example 2 are added in portions, with stirring, the reaction mixture being cooled, since the reaction is slightly exothermic. The resulting mixture is stirred overnight. 100 ml of a mixture of diethyl ether and water is then stirred in. The etheral phase is separated off, dried and concentrated to dryness, the residue being recrystallized from ethanol/petroleum ether. The product is subjected to fractional distillation and the residue is recrystallized from toluene/petroleum ether. The product obtained has a melting point of 48°–49° C.

EXAMPLE 8

Preparation of 1-phenyl-8-undecanoyloxyoctane-1,3-dione 11.7 g (0.05 mol) of the compound from Example 1, 10.0 g (0.05 mol) of lauric acid and 100 ml of toluene are heated under reflux for 1 hour in a 250 ml four-necked flask equipped with a water separator, a KPG stirrer, a thermometer, a reflux condenser and a bubble counter. No water of reaction can be detected, i.e. no reaction has taken place. After 0.3 g of para-toluenesulfonic acid has been added, the reaction mixture is again heated under reflux. After 3 hours 0.6 ml of water (calculated 0.9 ml) have been set free. The reaction mixture is cooled and washed with 50 ml of bicarbonate and 50 ml of water. The organic phase is dried and concentrated to dryness, the residue being recrystallized from a mixture of 140 ml of isopropanol and 10 ml of H$_2$O. The product obtained has a melting point of 37°–38° C.

EXAMPLE 9

The heat stability of polyvinyl chloride.

a) Static heat test

A dry mixture consisting of 100 parts of S-PVC (K-value 70), 17 parts of dioctyl phthalate, 3 parts of epoxidized soya-bean oil, 0.33 part of zinc oleate, 0.53 part of barium p-tert-butylbenzoate, 0.7 part of diisodecyl phenyl phosphite, 0.44 part of ®SHELL SOL A (mixture of aromatic hydrocarbons) and 0.2 part of stabilizer indicated in Table 2 is milled on mixing rolls for 5 minutes at 180° C. Samples of sheeting from the resulting rough sheet 0.3 mm thick are subjected to heat at 180° C. in a test oven (®Mathis Thermotester Type LTF-ST), and the "Yellowness Index" (YI) of a test sample is determined as specified in ASTM D 1925 at the interval of time indicated. The results are shown in Table 2.

TABLE 2

| Stabilizer | YI after oven aging in minutes | | | | | | |
|---|---|---|---|---|---|---|---|
| | 0 | 5 | 10 | 15 | 20 | 25 | 30 |
| without | 9.5 | 12.0 | 15.1 | 19.5 | 26.0 | 28.8 | 29.3 |
| compound of example 1 | 0.8 | 1.0 | 0.9 | 1.8 | 2.0 | 2.3 | 2.7 | b) Dynamic heat test

A dry mixture consisting of 100 parts of S-PVC, 1 part of polyacrylate (flow aid), 10 parts of methyl methacrylate/butadiene/styrene resin (impact modifier), 0.1 part of polyethylene wax, 1 part of ®Loxiol GH4 (lubricant), 1.43 parts of di-n-octyltin dipropanoate, 0.07 part of 2,6-di-tert-butyl-4-methylphenol, 1 part of epoxidized soya-bean oil, 0.1 part of Zn bis-(ethylhexanoate) and 0.5 part of the compound indicated in Table 3 is milled on mixing rolls at 190° C. Pieces of sheeting are taken out at regular intervals of time and their yellowing is determined as specified in ASTM D 1925. The results are shown in Table 3.

TABLE 3

| Stabilizer | YI after aging in minutes | | |
|---|---|---|---|
| | 5 | 10 | 15 |
| without | 22.8 | 52.7 | 82.4 |
| compound of example 1 | 3.3 | 5.6 | 9.5 |

We claim:
1. A composition containing
   a) a chlorine-containing polymer selected from the group consisting of a chlorinated vinyl resin and a chlorinated polyolefin resin and
   b) an effective stabilizing amount of a compound of the formula I

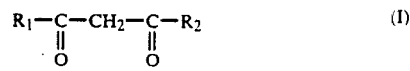

in which R$_1$ is C$_1$–C$_4$alkyl or phenyl and R$_2$ is C$_2$–C$_7$hydroxyalkyl or hydroxyphenyl, with the proviso that R$_2$ is not hydroxyphenyl when R$_1$ is phenyl.

2. A method for stabilizing a chlorine-containing polymer selected from the group consisting of a chlorinated vinyl resin and a chlorinated polyolefin resin against degradation by heat which comprises incorporating into said polymer an effective stabilizing amount of a compound of the formula I

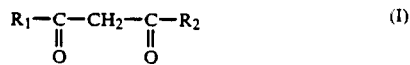

in which R$_1$ is C$_1$–C$_4$alkyl or phenyl and R$_2$ is C$_2$–C$_7$hydroxyalkyl or hydroxyphenyl, with the proviso that R$_2$ is not hydroxyphenyl when R$_1$ is phenyl.

3. A compound of the formula IA

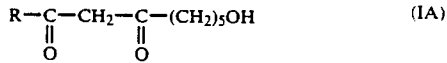

in which R is C$_1$–C$_4$alkyl or phenyl.

4. A composition according to claim 1, in which R$_2$ is a group —(CH$_2$)$_n$—OH in which n is an integer from 2 to 7.

5. A composition according to claim 1, in which R$_1$ is methyl, butyl or phenyl and R$_2$ is 2hydroxyethyl, 5-hydroxypentyl, 6-hydroxyhexyl, 7-hydroxyheptyl or ortho-hydroxyphenyl.

6. A composition according to claim 1, in which the compound of the formula I is 1-phenyl-8-hydroxyoctane-1,3-dione, 1-t-butyl-8-hydroxyoctane-1,3-dione or 1-(o-hydroxyphenyl)butane-1,3-dione.

7. A composition according to claim 1, in which the compound of the formula I is 1-phenyl-8-hydroxyoctane-1,3-dione.

8. A composition according to claim 1, in which the chlorine-containing polymer is polyvinylchloride.

9. A composition according to claim 1, containing, in addition, an epoxy compound and at least one Me(II) carboxylate and/or Me(II) phenate in which Me(II) is Ba, Ca, Mg, Cd or Zn.

10. A composition according to claim 1, containing, in addition, epoxidized soya-bean oil and at least one Me(II) carboxylate in which Me(II) is Ba, Ca, Mg or Zn.

11. A composition according to claim 9, containing, in addition, a phosphite.

12. A composition according to claim 1, containing, in addition, an organotin compound.

13. A compound according to claim 3, in which $R_1$ is phenyl.

14. The compounds 1-phenyl-8-hydroxyoctane-1,3-dione and 1-t-butyl-8-hydroxyoctane-1,3-dione according to claim 3.

* * * * *